US012281087B1

(12) United States Patent
Hessein et al.

(10) Patent No.: US 12,281,087 B1
(45) Date of Patent: Apr. 22, 2025

(54) EBSELEN ANALOGUES LOADED NANOEMULSION

(71) Applicant: KING FAISAL UNIVERSITY, Al-Ahsa (SA)

(72) Inventors: Manal Amin Hessein, Al-Ahsa (SA); Saad Shaaban, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 79 days.

(21) Appl. No.: 18/419,354

(22) Filed: Jan. 22, 2024

(51) Int. Cl.
| | | |
|---|---|---|
| *C07D 293/12* | (2006.01) | |
| *A61K 9/107* | (2006.01) | |
| *A61K 31/7135* | (2006.01) | |
| *A61K 47/26* | (2006.01) | |
| *A61K 47/44* | (2017.01) | |

(52) U.S. Cl.
CPC .......... *C07D 293/12* (2013.01); *A61K 9/1075* (2013.01); *A61K 31/7135* (2013.01); *A61K 47/26* (2013.01); *A61K 47/44* (2013.01)

(58) Field of Classification Search
CPC .................................................. C07D 293/12
See application file for complete search history.

(56) References Cited

U.S. PATENT DOCUMENTS

2019/0161482 A1* 5/2019 Sucheck .............. C07D 421/06

FOREIGN PATENT DOCUMENTS

| CN | 108484528 A | 9/2018 |
| WO | 2008123797 A1 | 10/2008 |

OTHER PUBLICATIONS

Shaaban et al., "Organoselenocyanates and symmetrical diselenides redox modulators: Design, synthesis and biological evaluation", European Journal of Medicinal Chemistry, vol. 97, Jun. 5, 2015, pp. 190-201.

* cited by examiner

*Primary Examiner* — Rei Tsang Shiao
(74) *Attorney, Agent, or Firm* — Nath, Goldberg & Meyer; Joshua B. Goldberg

(57) ABSTRACT

Ebselen analogue compounds, their synthesis, and nanoemulsions containing the same. The nanoemulsions can comprise the ebselen analogue, tea tree oil, Tween, and water.

18 Claims, No Drawings

EBSELEN ANALOGUES LOADED NANOEMULSION

BACKGROUND

1. Field

The present disclosure relates to certain ebselen analogues, their synthesis, and nanoemulsions containing the same.

2. Description of the Related Art

Ebselen is the most investigated heterocyclic-based organoselenium compound. It exhibits a wide range of biological activities such as anti-inflammatory, cytoprotective, antiviral, and anticancer activities. While these activities are generally referred to as glutathione peroxidase-like activities, the mode-of-action of ebselen is much more complex. Ebselen protects cells from oxidative stress and oxidative damage by neutralization of hydroperoxides.

Currently, ebselen is in different clinical trials for the management of different diseases including atherosclerosis and cardiovascular diseases. It is also proposed as a possible antiviral therapy against different viruses such as Zika, HCV, and HIV-1 viruses. Ebselen also was able to inhibit SARS-CoV-2 replication by inhibiting the $PL^{pro}$ and $M^{pro}$ proteases.

On the other hand, hydrophobic drugs represent a hot research area in a development stage to find a way to deliver incompatible hydrophobic drugs to pass through hydrophilic physiological barriers. This work remains ongoing.

Thus, new hydrophobic drugs and delivery systems for the same solving the aforementioned problems are desired.

SUMMARY

Presented herein is a facile, ecofriendly method of obtaining a nanoemulsion containing ebselen and/or its analogues, tea tree oil, and Tween by a high-speed shearing method. Tea tree oil is chosen based on its pharmacologic effects, including antifungal, anti-inflammatory, antibacterial, and immunomodulatory characteristics. The present nanoemulsions are capable of carrying the hydrophobic ebselen and/or analogues thereof using a hydrophilic carrier. The present nanoemulsions can be used for drug delivery and can provide several advantages such as high surface area and easy preparation methods.

In one embodiment, the present subject matter relates to an ebselen analogue compound having the formula:

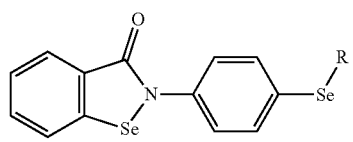

wherein R is selected from the group consisting of methyl, a $C_2$-$C_6$ alkenyl, methylphenyl, and

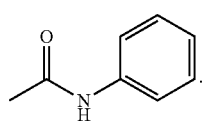

In another embodiment, the present subject matter relates to a pharmaceutically acceptable composition comprising a therapeutically effective amount of the ebselen analogue compound as described herein and a pharmaceutically acceptable carrier.

In a further embodiment, the present subject matter relates to a method of providing a pharmaceutical effect in a subject comprising administering to a subject in need thereof a therapeutically effective amount of the ebselen analogue compound as described herein.

In an additional embodiment, the present subject matter relates to a method of making the ebselen analogue compound described herein, the method comprising: adding, to a solution of anthranilic acid in HCl; $NaNO_2$ in water at a temperature of about 0.5° C. to obtain a diazonium chloride salt; adding the diazonium chloride salt to a $Na_2Se_2$ solution in water to obtain 2,2'-diselanediyldibenzoic acid; refluxing the 2,2'-diselanediyldibenzoic acid in $CH_2Cl_2$ using $SOCl_2$ to obtain 2-(chlorocarbonyl)phenyl hypochloroselenoite; reacting 2-(chlorocarbonyl)phenyl hypochloroselenoite with 4,4'-diselanediyldianiline in $CH_2Cl_2$ to obtain 2,2'-(diselanediylbis(4,1-phenylene))bis(benzo[d][1,2]selenazol-3(2H)-one); adding NaOH, an alkyl halide, and $NaBH_4$ to a solution of the 2,2'-(diselanediylbis(4,1-phenylene))bis(benzo[d][1,2]selenazol-3(2H)-one) in ethanol to obtain a reaction mixture while stirring; removing solvent from the reaction mixture under reduced pressure to obtain a residue; dissolving the residue in ethyl acetate followed by extraction with water; and obtaining the ebselen analogue compound.

In one more embodiment, the present subject matter relates to a method of making the ebselen analogue compound as described herein, the method comprising: adding NaOH, an alkyl halide, and $NaBH_4$ to a solution of 2,2'-(diselanediylbis(4,1-phenylene))bis(benzo[d][1,2]selenazol-3(2H)-one) in ethanol to obtain a reaction mixture while stirring; removing solvent from the reaction mixture under reduced pressure to obtain a residue; dissolving the residue in ethyl acetate followed by extraction with water; and obtaining the ebselen analogue compound.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Presented herein is a facile, ecofriendly method of obtaining a nanoemulsion containing ebselen and/or its analogues, tea tree oil, and Tween by a high-speed shearing method. Tea tree oil is chosen based on its pharmacologic effects, including antifungal, anti-inflammatory, antibacterial, and immunomodulatory characteristics. The present nanoemulsions are capable of carrying the hydrophobic ebselen and/or analogues thereof using a hydrophilic carrier. The present nanoemulsions can be used for drug delivery and can provide several advantages such as high surface area and easy preparation methods.

In one embodiment, the present subject matter relates to an ebselen analogue compound having the formula:

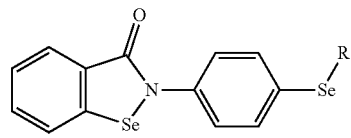

wherein R is selected from the group consisting of methyl, a $C_2$-$C_6$ alkenyl, methylphenyl, and

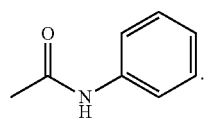

In an embodiment in this regard, the ebselen analogue compound can be selected from the group consisting of:

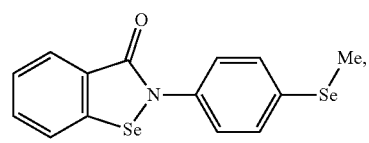

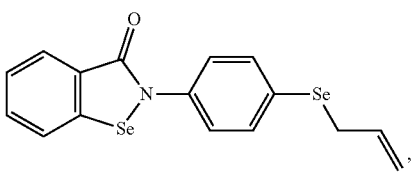

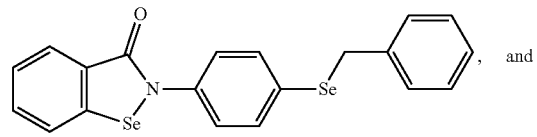

-continued

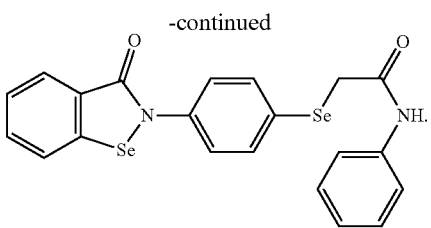

In another embodiment, the present subject matter relates to a pharmaceutically acceptable composition comprising a therapeutically effective amount of the ebselen analogue compound as described herein and a pharmaceutically acceptable carrier.

In an embodiment in this regard, the ebselen analogue compound present in the pharmaceutically acceptable composition can be selected from the group consisting of:

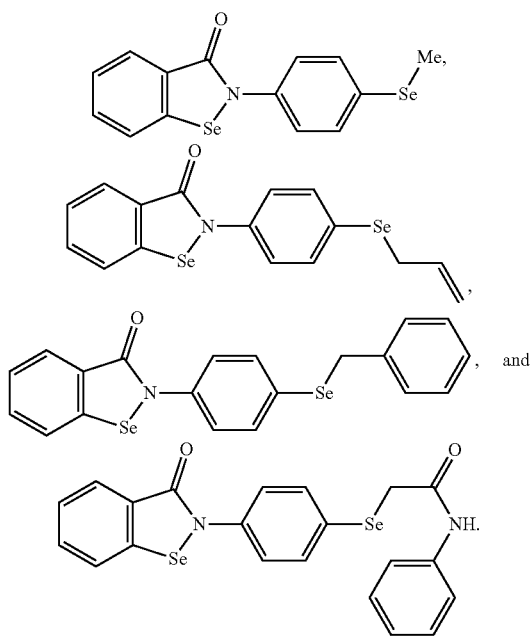

In other embodiments, the pharmaceutically acceptable composition can be formulated as a nanoemulsion. In this regard, the nanoemulsion can be an oil in water emulsion having the ebselen analogue compound in the oil phase of the oil in water emulsion. In certain embodiments, the nanoemulsion can comprise water, Tween 80, tea tree oil, and the ebselen analogue compound.

In certain embodiments, the ebselen analogue compound can be about 1% to about 4% of the oil phase of the oil in water nanoemulsion, by weight. In other embodiments, the nanoemulsion can comprise about 10% by weight of the ebselen analogue and oil, about 10% by weight of the Tween, and about 80% by weight of the water.

In a further embodiment, the present subject matter relates to a method of providing a pharmaceutical effect in a subject comprising administering to a subject in need thereof a therapeutically effective amount of the ebselen analogue compound as described herein.

In an embodiment in this regard, the pharmaceutical effect can be selected from the group consisting of an anti-inflammatory effect, a cytoprotective effect, an antiviral effect, an anticancer effect, an antioxidant effect, treatment of a cardiovascular disease, treatment of atherosclerosis, and combinations thereof.

The present compound is typically administered at a therapeutically or pharmaceutically effective dosage, e.g., a dosage sufficient to provide the desired pharmaceutical effect. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for providing a desired pharmaceutical effect, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols, or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum, and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In one embodiment, the present ebselen analogue compounds can be prepared according to the Scheme 1 below.

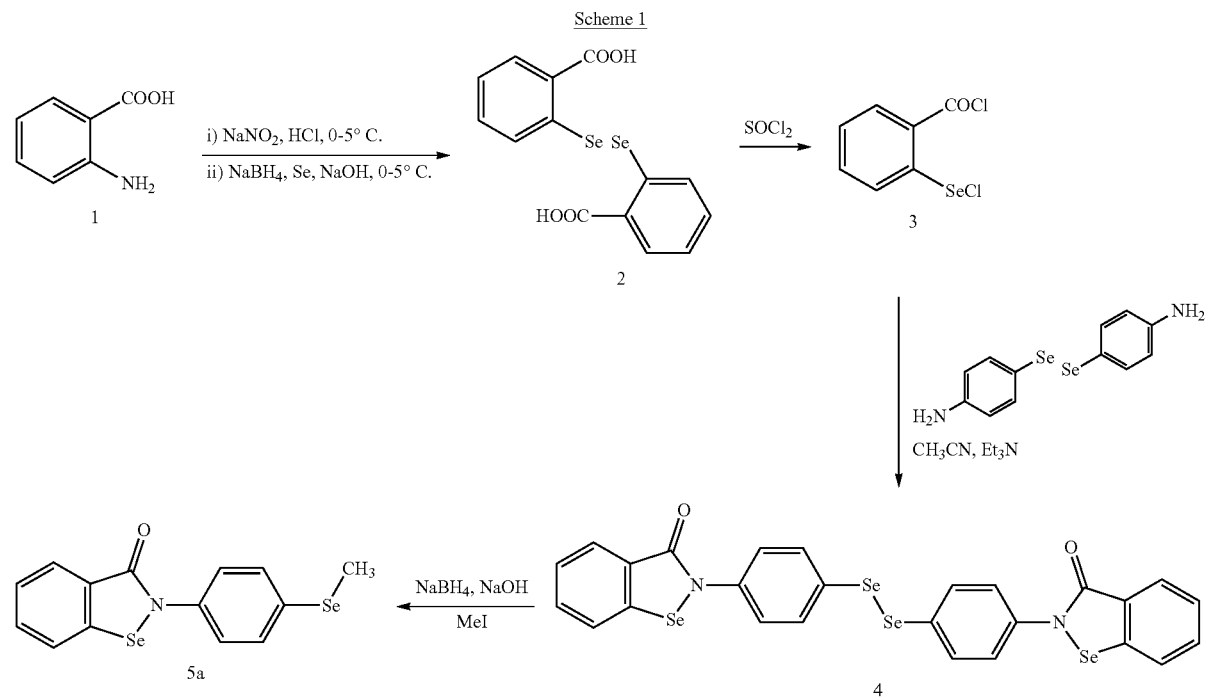

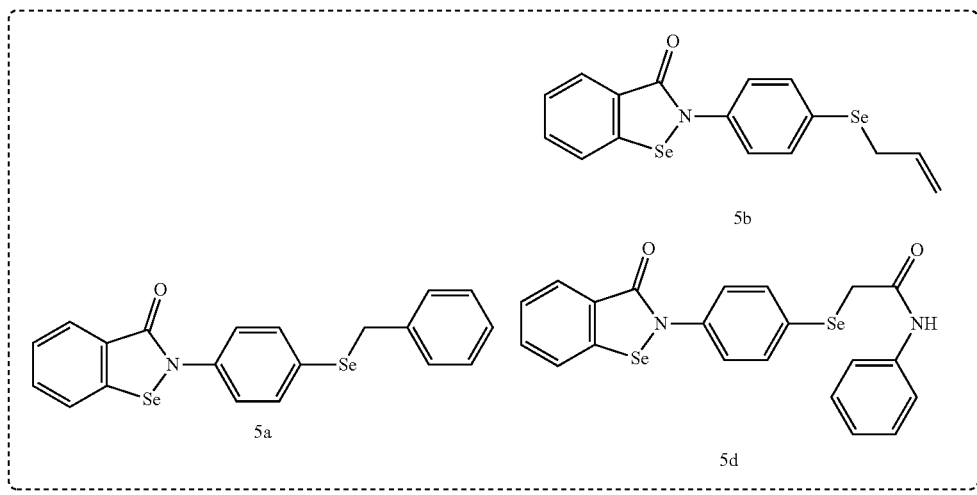

Accordingly, in an additional embodiment, the present subject matter relates to a method of making the ebselen analogue compound described herein, the method comprising: adding, to a solution of anthranilic acid in HCl; NaNO$_2$ in water at a temperature of about 0.5° C. to obtain a diazonium chloride salt; adding the diazonium chloride salt to a Na$_2$Se$_2$ solution in water to obtain 2,2'-diselanediyldibenzoic acid; refluxing the 2,2'-diselanediyldibenzoic acid in CH$_2$Cl$_2$ using SOCl$_2$ to obtain 2-(chlorocarbonyl)phenyl hypochloroselenoite; reacting 2-(chlorocarbonyl)phenyl hypochloroselenoite with 4,4'-diselanediyldianiline in CH$_2$Cl$_2$ to obtain 2,2'-(diselanediylbis(4,1-phenylene))bis(benzo[d][1,2]selenazol-3(2H)-one); adding NaOH, an alkyl halide, and NaBH$_4$ to a solution of the 2,2'-(diselanediylbis(4,1-phenylene))bis(benzo[d][1,2]selenazol-3(2H)-one) in ethanol to obtain a reaction mixture while stirring; removing solvent from the reaction mixture under reduced pressure to obtain a residue; dissolving the residue in ethyl acetate followed by extraction with water; and obtaining the ebselen analogue compound.

In one more embodiment, the present subject matter relates to a method of making the ebselen analogue compound as described herein, the method comprising: adding NaOH, an alkyl halide, and NaBH$_4$ to a solution of 2,2'-(diselanediylbis(4,1-phenylene))bis(benzo[d][1,2]selenazol-3(2H)-one) in ethanol to obtain a reaction mixture while stirring; removing solvent from the reaction mixture under reduced pressure to obtain a residue; dissolving the residue in ethyl acetate followed by extraction with water; and obtaining the ebselen analogue compound.

According to the present production methods, the NaOH, NaBH$_4$, and 2,2'-(diselanediylbis(4,1-phenylene))bis(benzo[d][1,2]selenazol-3(2H)-one) can be in the reaction mixture in a molar ratio of 1:3:1. Further, the reaction mixture can be stirred for about 2 hours. In an embodiment, the alkyl halide can be MeI.

The following examples relate to various methods of manufacturing the specific compounds and application of the same, as described herein. All compound numbers expressed herein are with reference to the synthetic pathway figures shown above.

EXAMPLES

Example 1

Synthesis of the Ebselen Analogues

To a solution of anthranilic acid (1, 1 mmol) in 2 ml conc. HCl, NaNO$_2$ (1.2 mmol, in 2 ml distilled water) was added while maintaining the temperature at 0.5° C. The in situ formed diazonium chloride salt was added to Na$_2$Se$_2$ solution (prepared from selenium powder (4.4 g,), NaBH$_4$ (4.4 g), and NaOH (2.2 g) in 15 ml of H$_2$O to give the respective 2,2'-diselanediyldibenzoic acid (2). The latter was refluxed in CH$_2$Cl$_2$ using SOCl$_2$ (5 ml) which in turn afforded 2-(chlorocarbonyl)phenyl hypochloroselenoite (3).

The reaction of 3 (2 mmol) with 4,4'-diselanediyldianiline (0.9 mmol) in CH$_2$Cl$_2$ (10 ml) and triethyl amine (0.5 ml) afforded 2,2'-(diselanediylbis(4,1-phenylene))bis(benzo[d][1,2]selenazol-3(2H)-one) (4).

Example 2

Synthesis of Compound 5a

To a solution of compound 4 (1 mmol) in 20 ml ethanol, NaOH (1 mmol), MeI (2.2 mmol), and NaBH$_4$ (3 mmol) were added, and the reaction mixture was stirred for 2 hrs. The solvent was then removed under reduced pressure and the residue was dissolved in ethyl acetate and extracted with H$_2$O.

The rest of the compounds were synthesized in a similar procedure by changing the alkyl halide.

Example 3

Preparation of the Ebselen Analogues Loaded Nanoemulsion

The reagents used for the preparation of the ebselen analogues loaded nanoemulsion (including potentially concentration ranges) include deionized water, Tween 80, Tea tree oil, and the Ebselen analogues (0.001-0.4 wt. %) of the total composition.

The ebselene analogues are 1-4% by weight of the oil phase. Further, the ebselen/Oil:Tween:water ratio by weight=10:10:80.

The hydrophobic phase containing the ebselen analogue, tea tree oil, and Tween was mixed under magnetic stirring at 500 rpm for 15 minutes. Then water is added and subjected to high shear by high-speed homogenizer at pressure 1000 bar.

It is to be understood that the ebselen analogue compounds, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An ebselen analogue compound having the formula:

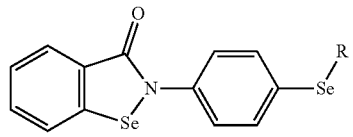

wherein R is selected from the group consisting of methyl, a $C_2$-$C_6$ alkenyl, methylphenyl, and

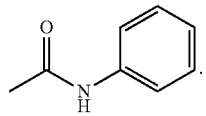

2. The ebselen analogue compound of claim 1, wherein the ebselen analogue compound is selected from the group consisting of:

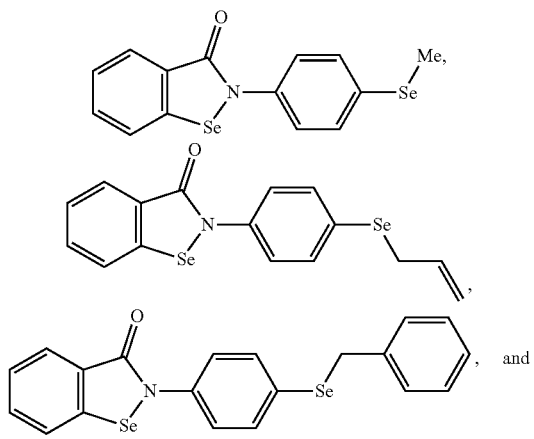

and

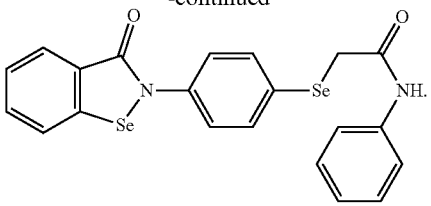

3. A pharmaceutically acceptable composition comprising a therapeutically effective amount of the ebselen analogue compound of claim 1 and a pharmaceutically acceptable carrier.

4. The pharmaceutically acceptable composition of claim 3, wherein the ebselen analogue compound is selected from the group consisting of:

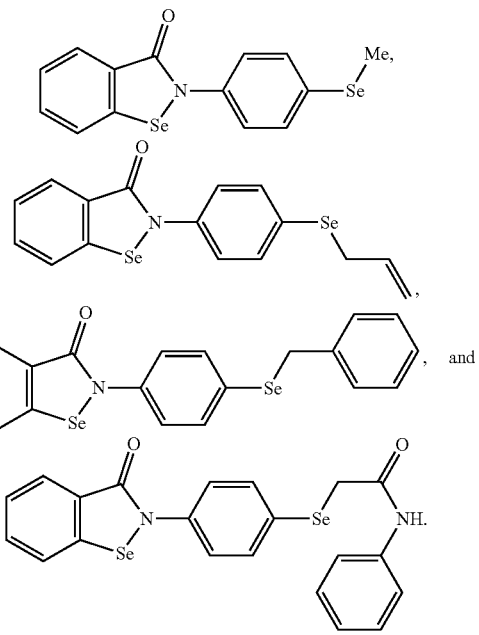

5. The pharmaceutically acceptable composition of claim 3, wherein the pharmaceutically acceptable composition is formulated as a nanoemulsion.

6. The pharmaceutically acceptable composition of claim 5, wherein the nanoemulsion is an oil in water emulsion having the ebselen analogue compound in the oil phase of the oil in water emulsion.

7. The pharmaceutically acceptable composition of claim 5, wherein the nanoemulsion comprises water, Tween 80, tea tree oil, and the ebselen analogue compound.

8. The pharmaceutically acceptable composition of claim 7, wherein the ebselen analogue compound is about 1% to about 4% of the oil phase, by weight.

9. The pharmaceutically acceptable composition of claim 7, wherein the nanoemulsion comprises about 10% by weight of the ebselen analogue and oil, about 10% by weight of the Tween, and about 80% by weight of the water.

10. A method of providing a pharmaceutical effect in a subject comprising administering to a subject in need thereof a therapeutically effective amount of the ebselen analogue compound of claim 1, wherein the pharmaceutical effect is selected from the group consisting of an anti-inflammatory effect, a cytoprotective effect, an antiviral effect, an anticancer effect, an antioxidant effect, treatment of a cardiovascular disease, treatment of atherosclerosis, and combinations thereof.

11. A method of making the ebselen analogue compound of claim 1, the method comprising:
   adding, to a solution of anthranilic acid in HCl; $NaNO_2$ in water at a temperature of about 0.5° C. to obtain a diazonium chloride salt;
   adding the diazonium chloride salt to a $Na_2Se_2$ solution in water to obtain 2,2'-diselanediyldibenzoic acid;
   refluxing the 2,2'-diselanediyldibenzoic acid in $CH_2Cl_2$ using $SOCl_2$ to obtain 2-(chlorocarbonyl)phenyl hypochloroselenoite;
   reacting 2-(chlorocarbonyl)phenyl hypochloroselenoite with 4,4'-diselanediyldianiline in $CH_2Cl_2$ to obtain 2,2'-(diselanediylbis(4,1-phenylene))bis(benzo[d][1,2]selenazol-3(2H)-one);
   adding NaOH, an alkyl halide, and $NaBH_4$ to a solution of the 2,2'-(diselanediylbis(4,1-phenylene))bis(benzo[d][1,2]selenazol-3(2H)-one) in ethanol to obtain a reaction mixture while stirring;
   removing solvent from the reaction mixture under reduced pressure to obtain a residue;
   dissolving the residue in ethyl acetate followed by extraction with water; and
   obtaining the ebselen analogue compound.

12. The method of making the ebselen analogue compound of claim 11, wherein the NaOH, $NaBH_4$, and 2,2'-(diselanediylbis(4,1-phenylene))bis(benzo[d][1,2]selenazol-3(2H)-one) are in the reaction mixture in a molar ratio of 1:3:1.

13. The method of making the ebselen analogue compound of claim 11, wherein the reaction mixture is stirred for about 2 hours.

14. The method of making the ebselen analogue compound of claim 11, wherein the alkyl halide is MeI.

15. A method of making the ebselen analogue compound of claim 1, the method comprising:
   adding NaOH, an alkyl halide, and $NaBH_4$ to a solution of 2,2'-(diselanediylbis(4,1-phenylene))bis(benzo[d][1,2]selenazol-3(2H)-one) in ethanol to obtain a reaction mixture while stirring;
   removing solvent from the reaction mixture under reduced pressure to obtain a residue;
   dissolving the residue in ethyl acetate followed by extraction with water; and
   obtaining the ebselen analogue compound.

16. The method of making the ebselen analogue compound of claim 15, wherein the NaOH, $NaBH_4$, and 2,2'-(diselanediylbis(4,1-phenylene))bis(benzo[d][1,2]selenazol-3(2H)-one) are in the reaction mixture in a molar ratio of 1:3:1.

17. The method of making the ebselen analogue compound of claim 15, wherein the reaction mixture is stirred for about 2 hours.

18. The method of making the ebselen analogue compound of claim 15, wherein the alkyl halide is MeI.

* * * * *